(12) United States Patent
Lazaro Flores et al.

(10) Patent No.: US 6,290,994 B1
(45) Date of Patent: Sep. 18, 2001

(54) BEVERAGE CONTAINING CAFFEINE OR THEOBROMINE AND VINPOCETINE CITRATE FOR STIMULATING CEREBRAL ACTIVITY

(75) Inventors: Consuelo Lazaro Flores; Paula Calvo Lazaro; Elena Calvo Lazaro; María Teresa Manresa Ferrero; Fernando Calvo Mondelo, all of Madrid (ES)

(73) Assignee: Decox, S.L., Madrid (ES)

( * ) Notice: Subject to any disclaimer, the term of this patent is extended or adjusted under 35 U.S.C. 154(b) by 0 days.

(21) Appl. No.: 09/654,332

(22) Filed: Sep. 1, 2000

Related U.S. Application Data

(63) Continuation of application No. 08/750,553, filed as application No. PCT/ES96/00082 on Apr. 10, 1996, now abandoned.

(30) Foreign Application Priority Data

Apr. 12, 1995 (ES) .................................................... 9500739

(51) Int. Cl.[7] ........................ A61K 35/78; A61K 47/00; A01N 43/42
(52) U.S. Cl. ........................ 424/725; 424/729; 424/774; 424/776; 424/777; 424/439; 514/283
(58) Field of Search ................................ 424/195.1, 439, 424/729, 774, 776, 777, 725; 514/283; 544/274, 275

(56) References Cited

U.S. PATENT DOCUMENTS

| | | | |
|---|---|---|---|
| 3,957,995 | 5/1976 | Amselem | 514/264 |
| 4,296,139 | 10/1981 | Khan et al. | 426/537 |
| 4,362,730 | 12/1982 | Kurt et al. | 514/283 |
| 4,749,707 | 6/1988 | Calvo et al. | 514/283 |
| 5,137,878 | 8/1992 | Pang et al. | 514/54 |
| 5,571,441 | 11/1996 | Andon et al. | 252/1 |

FOREIGN PATENT DOCUMENTS

| | | |
|---|---|---|
| 2559384 | 12/1975 | (DE) . |
| 2193586 | 2/1974 | (FR) . |
| 2193587 | 2/1974 | (FR) . |
| 2284325 | 4/1976 | (FR) . |
| 2319362 | 2/1977 | (FR) . |
| 2654119 | 6/1977 | (FR) . |
| 96749 | 4/1989 | (RO) . |

OTHER PUBLICATIONS

The Merck Index, 10th edition. (Merck: Rahway, NJ) (1983) p. 1428, 1429, 1327.

Iqbal et al. "The effect of caffeine on the Pharmacokietics of acetominophen in man," Biopharmaceutics and Drug Disposition (1995) 16:481–7.

Webster's II New Riverside University Dictionary, (1994) (Houghton–Mifflin: Boston) p. 589.

Kon et al. "The effect of ginseng saponins on microcirculation," Wakan Iyakugaku Zasshi (1994) 11(4):273–6 (abstract only).

Kumukov, A.G. "Effect of vincamine on the central nervous system," Farmakol. Alkaloidov, Serdechnykh Glidozidov (1971) p. 23–26 (abstract only).

*Primary Examiner*—David M. Naff
*Assistant Examiner*—Mike Meller
(74) *Attorney, Agent, or Firm*—Ostrolenk, Faber, Gerb & Soffen, LLP

(57) ABSTRACT

A beverage such as coffee, tea, cocoa or cola soda is described. The beverage contains caffeine or theobromine and between 0.5 and 30 mg of vinpocetine citrate per 100 ml of the beverage. The beverage is used to stimulate cerebral activity.

2 Claims, No Drawings

BEVERAGE CONTAINING CAFFEINE OR THEOBROMINE AND VINPOCETINE CITRATE FOR STIMULATING CEREBRAL ACTIVITY

This is a continuation of application Ser. No. 08/750,553, filed Jan. 22, 1997, now abandoned, which is based upon PCT International Application No. PCT/ES96/00082, filed Apr. 10, 1996, which claims priority of Spanish Application No. 9500739, filed Apr. 12, 1995.

TECHNICAL BACKGROUND OF THE INVENTION

The present invention relates to a new composition which stimulates cerebral activity, based on the discovery of the powerful action which certain eburnamenine ring alkaloids have when they are administered together with compounds of xanthine structure.

PRIOR ART

In general, the alkaloids of eburnane skeleton are peripheral vasodilators which are widely known (U.S. Pat. No. 4,400,514, Spanish Patent 549,105), which act as cerebral oxygenators Drug Res. [26(10a): 1947–1989 (1976)], and as memory activators [Drug Res. 26(10a):1947–1950 (1976); Eur. J. Clin. Pharmacol. 28:567–571 (1985); Drug Rev. Res. 14:191–193 (1988); Inter. Clin. Psychopharmacology 2:325–331 (1987)]. Furthermore, addition salts of eburnates are known which have properties similar to them or greatly improved properties and which furthermore are soluble in aqueous solutions from which potable solutions can be prepared; by way of example, it is sufficient to cite the citrate of vinpocetine [EP Patent 0154756], a cerebral oxygenator and vasodilator which has a better bioavailability and less toxicity than vinpocetine, its starting base.

With respect to the xanthic bases, we may cite, among the best known, theobromine which acts, among other things, as a cardiotonic [A. Lelo et al.: Brit J. Clin. Pharmacol. 22:177 (1986)]. Another interesting xanthine base is propentophylline, which acts as peripheral and cerebral vasodilator [K. Nagata et al.: Arzneimittel Forsch. 35:1034 (1985)] and as adenosine inhibitor [B. B. Fredheim et al.: Acta Pharmacol. Toxicol. 58:187 (1988)] and as cognitive activator [I. Hindmarch, Z. Subhan, Ibid. 5:379 (1985)], among others. Theophylline is a cardiac stimulant and muscular relaxant [(J. L. Cohen, *Analytical Profiles of Drug Substances*, Vol 4, K. Florey, Ed., Academic Press (N.Y.), p. 466–493 (1975)]. Finally, caffeine is a widely known general stimulant which is extracted from tea and coffee.

DESCRIPTION OF THE INVENTION

It has been known for some time that extracts of decoctions of certain plants such as coffee, tea, cocoa and ginseng, both that coming from Korea and that coming from Manchuria in their different species, white or red, such as the so-called Siberian ginseng (*Eleoterococcus senticosus*), including the oral administration of the plant itself as found in nature or ground with some processing, have a characteristic tonic and stimulating effect which results in a general invigorating of the physical condition and a parallel stimulating action of mental activity, which, depending on the plant in question, is more or less pronounced, on some of the feelings of physical well-being and/or mental alertness which are produced with a greater and more substantial action depending on the vegetable species.

The duration and intensity of the stimulating effect on the central nervous system (CNS) can be obtained, both in the short term and in the long term, depending on the concentration of the extract or species of plant used and, in the final analysis, depending on the amount and combination of active principles which are contained in the plant.

The popular and in some cases medical use of these compounds in their different forms has been known for many years and there have also been known certain side effects which at times are undesirable which exist such as the insomnia produced in certain individuals by coffee, or in a certain degree of nervousness in some persons who are very sensitive to chocolate.

In each case, these effects are taken into account, which does not prevent the daily use of these products which have an undeniable popularity throughout the different areas of the world.

In some countries, coffee is used more in all its varieties, such as arabica or robusto, while in other countries tea, from green tea in Japan and China to the innumerable varieties of tea of India or Europe or Arabia, is used most.

Chocolate and cocoa derivatives are widely used in the Orient as stimulants of physical and psychic vigor.

There is extensive scientific literature, both chemical as well as pharmacological and medical, as well as traditional literature, which can illustrate what has been stated above, but we shall not make reference thereto due to the great length which such a bibliography would require.

We believe that there is a great need for a composition which can be administered as a beverage, which has a stimulating effect on the central nervous system, in particular, stimulating the memory and the cognitive activity, but which has fewer undesired side effects than those observed with the customary beverages of daily consumption. In other words, beverages which can potentiate the stimulating effect, but reduce the undesired effects.

The active ingredients which are responsible for the stimulating effects have in general been widely identified so that it is known that caffeine is one of the principal activators of the mental alertness and well-being produced by coffee or tea, and theobromine is responsible for the effect of cocoa and derivatives of chocolate.

The action found has been attributed to these xanthic bases, and even theophylline, which is very closely related to caffeine and theobromine, is a member of this basic xanthic structure which has closely related properties.

Furthermore, it has been seen that the compounds obtained by synthesis exhibit a large part of the properties of the natural extracts, the dosing of their administration being in some cases easier.

The ginsenocides responsible for the invigorating caused by the administration of ginseng in its various forms and formulations have also been identified.

It may even be said that there is a large scientific arsenal which explains and lists the active principles which are produced by synthesis or are found in nature, as well as their pharmacological activity.

Furthermore, the properties of the alkaloids of eburnamenine structure are known for their interesting effects on the cerebral circulation, the cerebral vascular resistance in the cerebral vessels and their activity of increasing cerebral metabolism, which can be quantified by the increase in the consumption of glucose by the nerve cells as well as its greater resistance to cerebral hypoxia. Among the alkaloids used in therapy which correspond to this group, we may mention vinpocetine, vincamine, bromovincamine, eburnamonine or vincamone, among others, which are used with great success in the treatment of the deterioration of the cognitive functions in cerebral vascular problems, which arise in general in persons of advanced age.

The inventors have recently encountered an unexpected result after the oral administration to healthy volunteers of different ages of these traditional beverages combined with the compounds of eburnamenine ring mentioned. This effect has been obtained and optimized by using different relative concentrations of the components, that is to say by effecting a gradation of the concentrations of the xanthic bases used and the eburnamenine ring derivatives in the case of coffee, cocoa or tea, or dosing the theophylline in the case of its use as component or else dosing the concentration of the natural ginsenocides or the concentrations of active principles of *Eleteorococus senticosus* in the case of the different ginseng extracts used.

This marked and unexpected powerful synergistic effect is obtained in all cases with the different concentrations or relative contents used in each case, and in this way there can be observed a possible adaptation of the optimum concentration to the individual need measured as response in mental alertness or in the increase in cognitive capacity or else in the extent of the reduction or absence of the undesired effects.

Also, by the present invention there can be obtained compositions which give rise to effects more in the short term or more in the long term, it being possible, therefore, to use these compositions in the form of beverages in a rational manner, stimulating the activity and vigor, both physical and cerebral, in the short, medium or long term, selecting the optimum effect in accordance with the need and particular sensitivity to the composition.

In order to attempt to explain these effects, which seem to result in the short term and have a duration also in medium and long term, reference has been had to a number of hypotheses centered generally on the existing basic knowledge of the biochemistry of the nerve cells.

We will now explain briefly a few facts and possible explanations of this resultant synergistic phenomenon.

Thus, for example, it is known that vinpocetine increases or inhibits the formation of phosphodiesterase PDE, as theophylline also does to a lesser extent. Other xanthines, such as caffeine or theobromine, may also do so.

Adenyl cyclase acts on acid adenosine monophosphate (AMP) producing cyclic adenosine monophosphate (C-AMP) which, by the action of the PDE, liberates the AMP again (see French Patent 80 17165, Publication No. 2469180). Therefore, if theophylline inhibits the action of phosphodiesterase and therefore inhibits the formation of C-AMP and vinpocetine also does so, there is an interesting synergistic effect to be considered and used in order to activate the cerebral activity as a whole. This can be excellently measured by the methods described in the literature (Biochem. Biophys. Acta 302:50/1973, etc.) on papillae of animal tissues, for instance rat brains, and the inhibiting effect of different concentrations of purified enzyme (PDE) with respect to the C-AMP of the substrate, determinable quantitatively, can be tabulated and measured perfectly. If vinpocetine is added to the different solutions of varied concentration of PDE, it can be seen how it surprisingly acts, showing a clear inhibition of the enzymatic activity of the PDE on the reference substrate. In conclusion, this synergism can be used since, due to it, the AMP increases at the expense of C-AMP, it being possible to have a larger energy contribution coming from the ATP which is formed due to the greater availability of non-cyclic AMP, which permits a substantial increase in the intracellular metabolic processes and, in particular, those of the neuron cell with the consequent increase in the consumption of glucose and the placing in operation of the biochemical processes of mobilization of fats and utilization of the glucose available so as to have a larger contribution of the energy necessary to accelerate, activate or implement these processes in which precisely in the brain the energy sources are made very limited in order that the source of energy coming from the mobilizable polysaccharides is limited and in any event controlled by a very precise mechanism for the obtaining of them.

The ATP produced in this way is the source of energy which can be used for the cerebral biochemistry.

Among other eburnanes, vinpocetine has shown to also increase the levels of noradrenaline and dopamine in the brain.

We activate precisely the transmitters specifically entrusted with the cerebral biochemistry and, combining this with the greater obtaining of cell oxygen contributed by the demonstrated antihypoxic action of vinpocetine, measurable data can be obtained by experimentation, such as the measurement of the increase in the cerebral concentration of serotonin (5HT), released thus as well as a clear increase of its metabolite, 5-hydroxy-indoleacetic acid (5HIAA). This effect is maximum between 2 and 4 hours after administration.

The use of the synergistic mode of the xanthic bases described and an alkaloid of the eburnane type, for instance, vinpocetine citrate, which are administered orally, finally causes an increase in the concentration of neurotransmitters and an increase in ATP, which gives rise to an effective alteration of the cerebral metabolism which is quantifiable subjectively and objectively.

We may recall that it has been shown that compounds such as vinpocetine, theophylline and papaverine inhibit the PDE, while norepinephrine stimulates the adenyl cyclase, with the consequent effects on the concentrations of AMP.

It can be said that we obtain parallel phenomena by inhibiting the PDE or stimulating the function of the adenyl cyclase (ADC) with respect to the mobilization or immobilization of the AMP in accordance with the scheme: AMP→C-AMP→AMP and, parallel with this, AMP→ATP→ENERGY+AMP→ATP, etc.

These phenomena make it possible to assume that they increase the consumption of glucose in the brain and that they activate the cerebral metabolism, as can be determined, thanks to the modern techniques of cerebral scanning, when applied to persons carrying out given cerebral functions after the consumption of the beverages which are presented, for suitable periods of time as compared with the untreated subjects.

EMBODIMENTS OF THE INVENTION

A better understanding of the procedure of the invention will be obtained from the non-limitative examples of preparation which are set forth below.

EXAMPLE 1

In a mixer suitable for this purpose, there are suitably mixed 100 L of cola soda and 3.2 g of vinpocetine phosphate. The mixture is solubilized and suitably homogenized. Thereupon, the content is analyzed and adjusted so that every 100 ml of beverage contains 3.2 mg of vinpocetine, and is bottled.

EXAMPLE 2

In a mixer suitable for this purpose, there are suitably mixed 200 L of lemon soda and 50 L of aqueous solution containing 7.75 g of vinpocetine citrate. The mixture is suitably homogenized, its content being analyzed and adjusted so that every 125 ml of beverage contains 3.85 mg of vinpocetine citrate.

EXAMPLE 3

In a mixer suitable for the purpose, there are suitably mixed 200 L of chocolate soda and 3.2 g of vinpocetine sulfate. The mixture is solubilized and suitably homogenized. The content is then analyzed and adjusted so that every 200 ml of chocolate soda contains 3.2 mg of vinpocetine sulfate.

EXAMPLE 4

In a mixer/homogenizer suitable for the purpose, there are advisedly mixed 500 kg of dry ground or non-ground coffee extract with 250 g of vinpocetine citrate, obtaining good homogenization. This mixture is subsequently packed in individual-portion hermetic envelopes or air-tight containers of plastic and/or aluminum, in the absence of moisture, which contain the weight suitable for an individual portion and there are thus obtained containers of an approximate net weight of 5 g each, to which there can be added approximately 150 to 200 ml of water in order to obtain a beverage having the taste of coffee and to which sugar or sweeteners or taste enhancers may be added.

EXAMPLE 5

In a mixer suitable for this purpose, there are mixed and homogenized 200 kg of water-soluble defatted cocoa powder with 35 g of vinpocetine sulfate, thus obtaining a homogeneous powder which can be packed in a manner similar to that described in the preceding example. Upon mixing a single portion of approximately 20 g with 150 to 200 ml of hot or cold water, a chocolate-flavored beverage is obtained to which sugar or sweetener can be added.

EXAMPLE 6

In a mixer suitable for this purpose, there are mixed and homogenized 200 kg of defatted cocoa powder extract with 150 g of vinpocetine alpha-acetoglutarate until obtaining a homogeneous mixture, which is then packed in air-tight envelopes in the absence of moisture, each small envelope containing about 20 g, which envelopes can be used to prepare a glass of cocoa beverage.

EXAMPLE 7

In a mixer suitable for the purpose, 100 kg of extract of tea of any variety, from the green tea customarily used in Japan to the Oolong tea of China or the black tea of India or any tea for infusions from among those customary on the market, are suitably mixed with 100 g of vinpocetine citrate which is then packed and used in the manner described in the preceding examples, using water preferably in the final beverage.

EXAMPLE 8

In a mixer similar to those used in the preceding examples, 300 kg of dried ginseng extract are mixed with 350 g of vinpocetine citrate, thereupon packed in a manner similar to that explained in Examples 4, 5 and 6.

EXAMPLE 9

In an emulsion homogenizer of the type used in the chocolate industry for the preparation of melted cocoa, 20 kg of concentrated cola extract and 3 g of vinpocetine phosphate are placed and the homogenizer spun until a homogeneous mass is obtained. The mass is packed in plastic receptacles and can be stored for one year without its organoleptic and chemical properties changing. This extract can be used in order to add water, diluting it approximately to 100 times its volume and it may also be sweetened or sugared, thus preparing a cola beverage which can be carbonated at the time of its packing.

EXAMPLE 10

50 kg of powdered ginseng root and 35 g of vinpocetine citrate are suitably mixed in a homogenizer. It is packed in air-tight receptacles in such a manner that a beverage can be prepared with a teaspoonful of this mixture added to a cup of hot water, and stirring it in order to dissolve the powder suitably. Sweetener may be added, if desired.

EXAMPLE 11

Similar to what has been described in Example No. 4, but using decaffeinated coffee extract.

EXAMPLE 12

In a mixer suitable for the purpose, 200 liters of tonic water beverage are suitably mixed with 3.2 g of vinpocetine hydrochloride until completely dissolved. A tonic beverage is thus obtained. A small dose of theophylline or its pharmacologically acceptable salts may be added in order to potentiate its effects.

EXAMPLE 13

In a manner similar to the preceding example, but in this case using a beverage having a base of plant extracts of those commonly known in Spain as BITTER, having a characteristic bitter taste, is prepared.

EXAMPLE 14

In a receptacle there are placed with agitation 200 L of diluted cola extract having a base of cola extracts from among those commonly found on the soft-drink market and there are added thereto 2.5 liters of purified, concentrated extract of vinca minor or dehydrogenated extract of Crioceras longiflorus (apocinaceae). This is stirred and water then added until the concentration of alkaloids is brought to 15 mg per 100 ml. This determination is carried out by the customary technique of analytical determination of these alkaloids (for example, quantitative HPLC). The solution thus obtained can be carbonated with carbon dioxide and bottled, in a manner similar to that commonly used in the soft-drink industry, in containers of glass or aluminum covered by a layer of plastic on the inside, or in a "tetra-brick" container, that is to say of cardboard laminated with plastic on the inside, or in containers of tin plate duly treated in the manner used in the fruit-juice industry. Its capacity must be indicated on the container after the suitable stability tests at room temperature and accelerated aging, as is prescribed in the industry for this purpose.

All the above examples are merely illustrative of the invention and in no case limitative. In parallel, a stability study was carried out on the resultant beverages, verifying that both the organoleptic properties and the product, the addition salt of vinpocetine, or the eburnane extract, are stable within the margin of stability defined for each type of beverage.

What is claimed is:

1. A beverage consisting essentially of coffee, tea, cocoa or cola soda containing caffeine or theobromine and between 0.5 and 30 mg of added vinpocetine citrate per 100 ml of said beverage.

2. The beverage of claim 1, wherein the beverage is cocoa containing theobromine.

* * * * *